Figure 1:
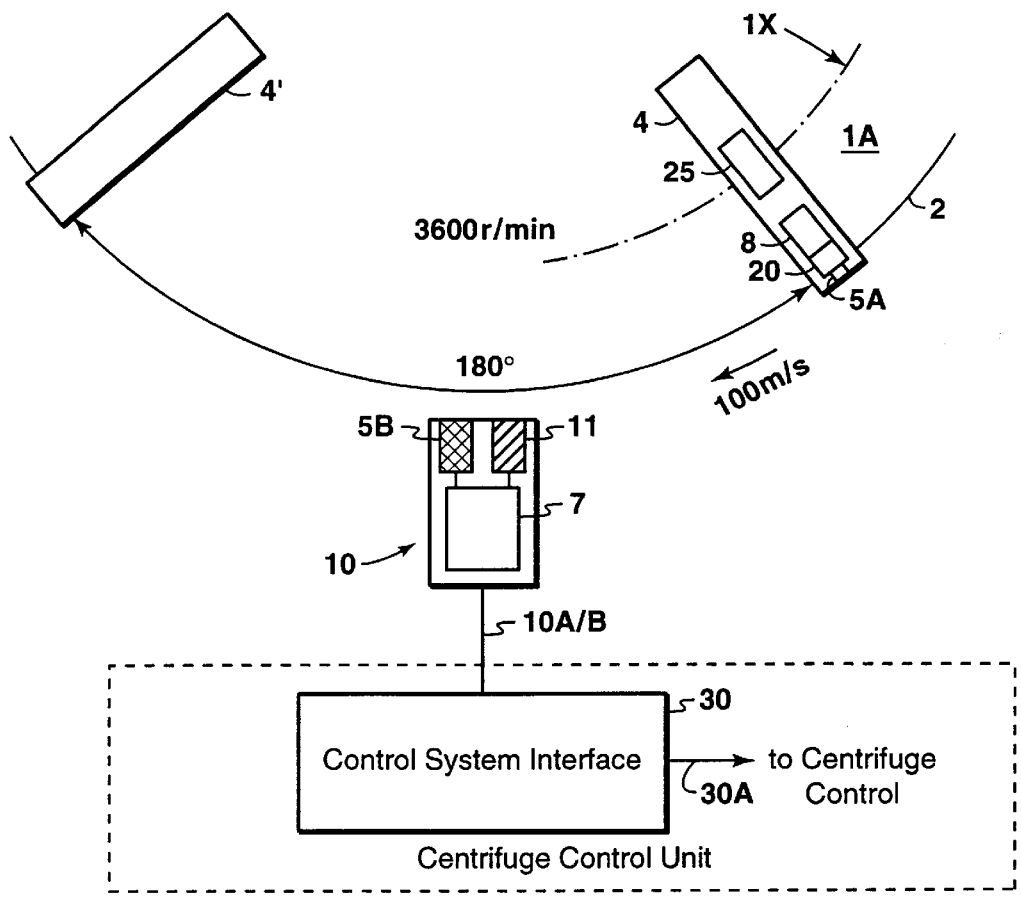

United States Patent [19]
Tonnesen et al.

[11] Patent Number: 6,011,490
[45] Date of Patent: *Jan. 4, 2000

[54] MEASURING APPARATUS

[75] Inventors: Harald Tonnesen, Stavanger; Per Scholberg Henriksen; Truls Fallet, both of Oslo, all of Norway

[73] Assignee: Exxon Production Research Company, Houston, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/860,156

[22] PCT Filed: Dec. 20, 1995

[86] PCT No.: PCT/NO95/00238

§ 371 Date: Sep. 12, 1997

§ 102(e) Date: Sep. 12, 1997

[87] PCT Pub. No.: WO96/19292

PCT Pub. Date: Jun. 27, 1996

[30] Foreign Application Priority Data

Dec. 21, 1994 [NO] Norway ..................... 944975

[51] Int. Cl.⁷ .................................. B04B 15/00
[52] U.S. Cl. .................. 340/870.3; 340/870.01; 340/870.16; 340/603; 494/10; 494/27
[58] Field of Search ............... 340/870.17, 870.18, 340/870.25, 870.26, 870.3, 870.39, 870.01, 531, 603, 870.16; 494/3, 10, 27, 37, 45, 17

[56] References Cited

U.S. PATENT DOCUMENTS

| | | | |
|---|---|---|---|
| 3,713,124 | 1/1973 | Durland et al. | 340/870.17 |
| 3,986,663 | 10/1976 | Jonsson et al. | 494/3 |
| 4,421,503 | 12/1983 | Latham | 494/17 |
| 4,557,719 | 12/1985 | Neumann et al. | 494/37 |
| 4,846,780 | 7/1989 | Galloway et al. | 494/3 |
| 4,900,453 | 2/1990 | Sedlmayer | 210/742 |
| 4,972,110 | 11/1990 | Gorodissky | 310/68 E |

FOREIGN PATENT DOCUMENTS

| | | | |
|---|---|---|---|
| 0 111 353 A2 | 6/1984 | European Pat. Off. | E21B 47/04 |
| 0 595 550 A1 | 4/1994 | European Pat. Off. | G01P 3/44 |
| 653 129 A5 | 12/1985 | Switzerland | G01F 23/26 |

*Primary Examiner*—Michael Horabik
*Assistant Examiner*—Albert K. Wong

[57] ABSTRACT

Apparatus for measurement concerning fluids in a rotor or container (2) during rotation, comprising an electric or magnetic sensor (4) mounted internally on a wall in the container (2), and means (5A, 5B) for contact-free and intermittent transmission of measurement signals from the sensor (4) to a stationary measuring unit (7) outside the container. The sensor (4) comprises an active electronic circuit (8) adapted to store measurement values that are recorded during at least a portion of a revolution of the container (2), before said transmission of corresponding measurement signals to the measuring unit (7). Electric power supply to the electronic circuit (8) is provided for by generator means comprising a stationary magnet (11) near the container (2) and a coil (12) mounted in the container so that a voltage is induced in the coil (12) during movement past the magnet (11) during the rotation of the container (2).

12 Claims, 5 Drawing Sheets

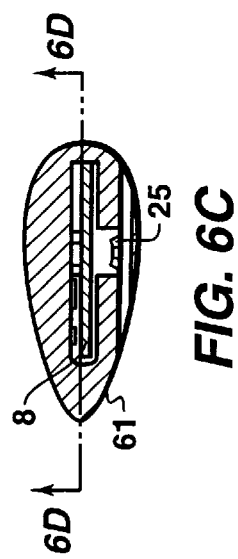
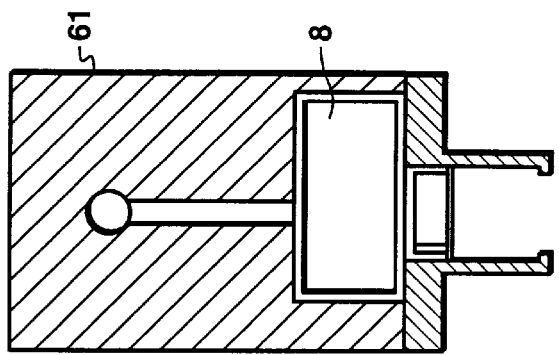
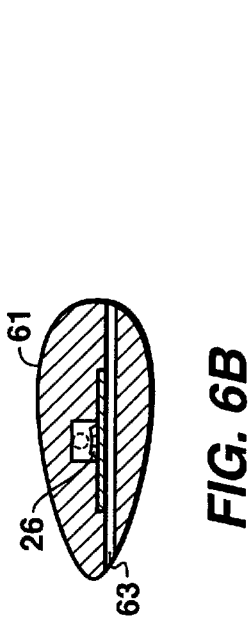
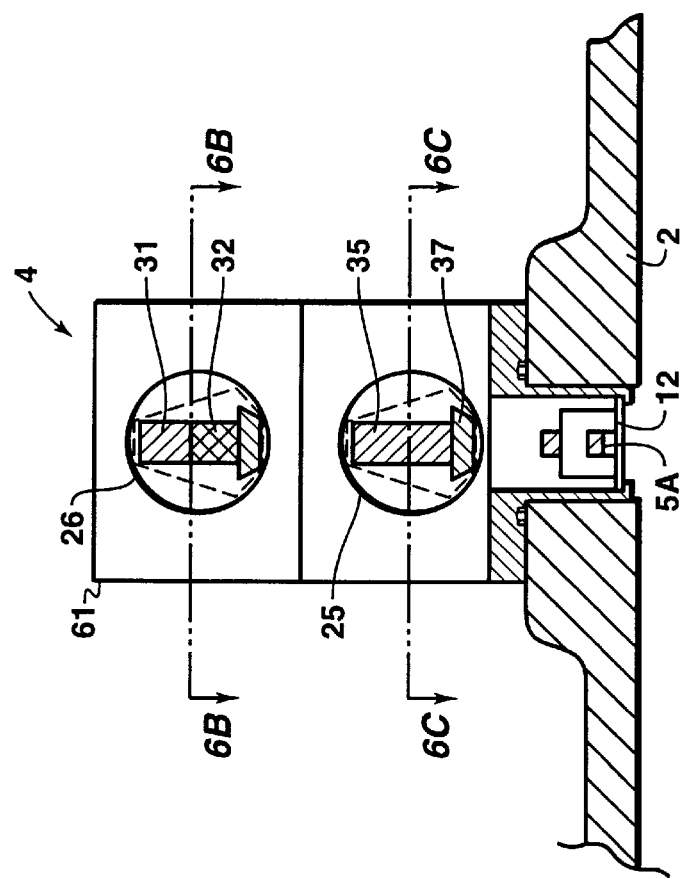

MEASURING APPARATUS

This invention relates to an apparatus for measurement of the position of an interface between two fluids in a centrifuge rotor during rotation, comprising an electric or magnetic sensor mounted internally on a wall in the centrifuge rotor, and means for contact-free and intermittent transmission of measurement signals from the sensor to a stationary measuring unit outside the centrifuge rotor.

Of particular interest to this invention is measurement in centrifuges for the separation of fluids obtained when producing oil from subsurface formations, including offshore oil production. In many cases during such production there will also be obtained water and gas together with the oil. In centrifuges used for separation of the fluid fractions it is of great importance to be able to measure the level of the water layer and the oil layer in the centrifuge rotor, i.e. in relation to the interior wall of the rotor. A high degree of accuracy is desired in this level measurement, i.e. measurement of the position of the interface between the fluids or media. Specifically it is important to be able to measure the position of the interface between water and oil with high accuracy.

Accurate measurement of position or level in this connection has been found to be difficult however, because of sources of error and disturbance factors, perhaps in particular the fact that the level of the interface of interfaces in a centrifuge rotor during rotation, may vary somewhat such as in consequence of the through-flow of fluids in the axial direction of the rotor. Also other factors can have influence on the measurement, for instance a varying salinity of the water, capillary effect and so forth. These factors or circumstances may be influenced either in a favourable or in an unfavourable direction under the high acceleration forces to which the fluids are subjected in the centrifuges concerned, for example 3000 G. Another consideration of significance is the response time for the measurements, since quick changes of the interface level in the centrifuge rotor may require quick adjustment or other precautions from an operator or a surrounding system.

From Swiss patent specification 653,129 there is known a measurement apparatus as stated in the introductory paragraph above. This known apparatus, however, will not result in sufficiently accurate measurement as required according to the above discussion, especially not in view of the disturbing factors or circumstances mentioned.

Moreover reference can be made to German patent specification 2.914.423 relating to a sentrifuge with means for optical measurements through cells incorporated in the sentrifuge rotor. There are also shown indications outside the sentrifuge rotor for measuring or controlling the rotational velocity of the rotor.

What is novel and specific in the apparatus according to the invention in the first place consists therein that the sensor has such an extension in the radial direction of the rotor that the sensor penetrates said interface, that the sensor comprises an active electronic circuit adapted to store measurement values that are recorded during at least a portion of a revolution of the rotor, before said transmission of corresponding measurement signals to the measuring unit, and that electric power supply to the electronic circuit is provided for by generator means comprising a stationary magnet near the centrifuge rotor and a coil mounted in the rotor so that a voltage is induced in the coil during movement past the magnet by rotation of the rotor, and the coil is connected to the electronic circuit.

A substantial advantage of the solution stated here, consists therein that the measurement can represent an average of level values over a portion of a revolution of the rotor or the container, or possibly several revolutions. This can be a fraction of a revolution, but normally in practice it will be convenient to transmit measurement signals to the measuring unit once for each revolution of the centrifuge rotor. The invention makes it possible to measure the position of the interface between water and oil with an accuracy at the order of magnitude of 0.1 mm.

As regards the basic principle of measurement in the sensor, this may be a capacitive measurement principle, as in the above mentioned Swiss patent specification, or the measurement may be based on other physical parameters, such as magnetic properties of the fluids concerned.

Although the primary and particularly interesting use of the invention relates to centrifuges for oil separation, also other fluids may be of interest.

Figure 3:
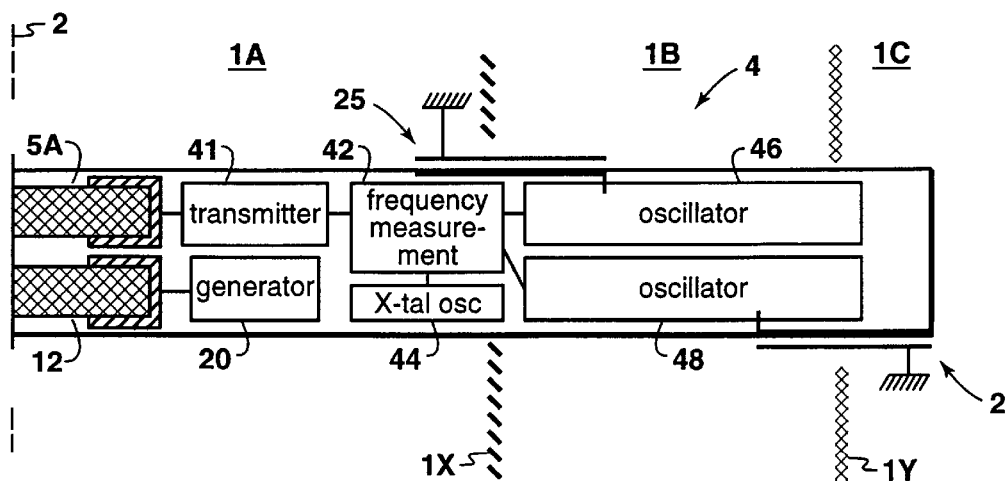
Figure 2:
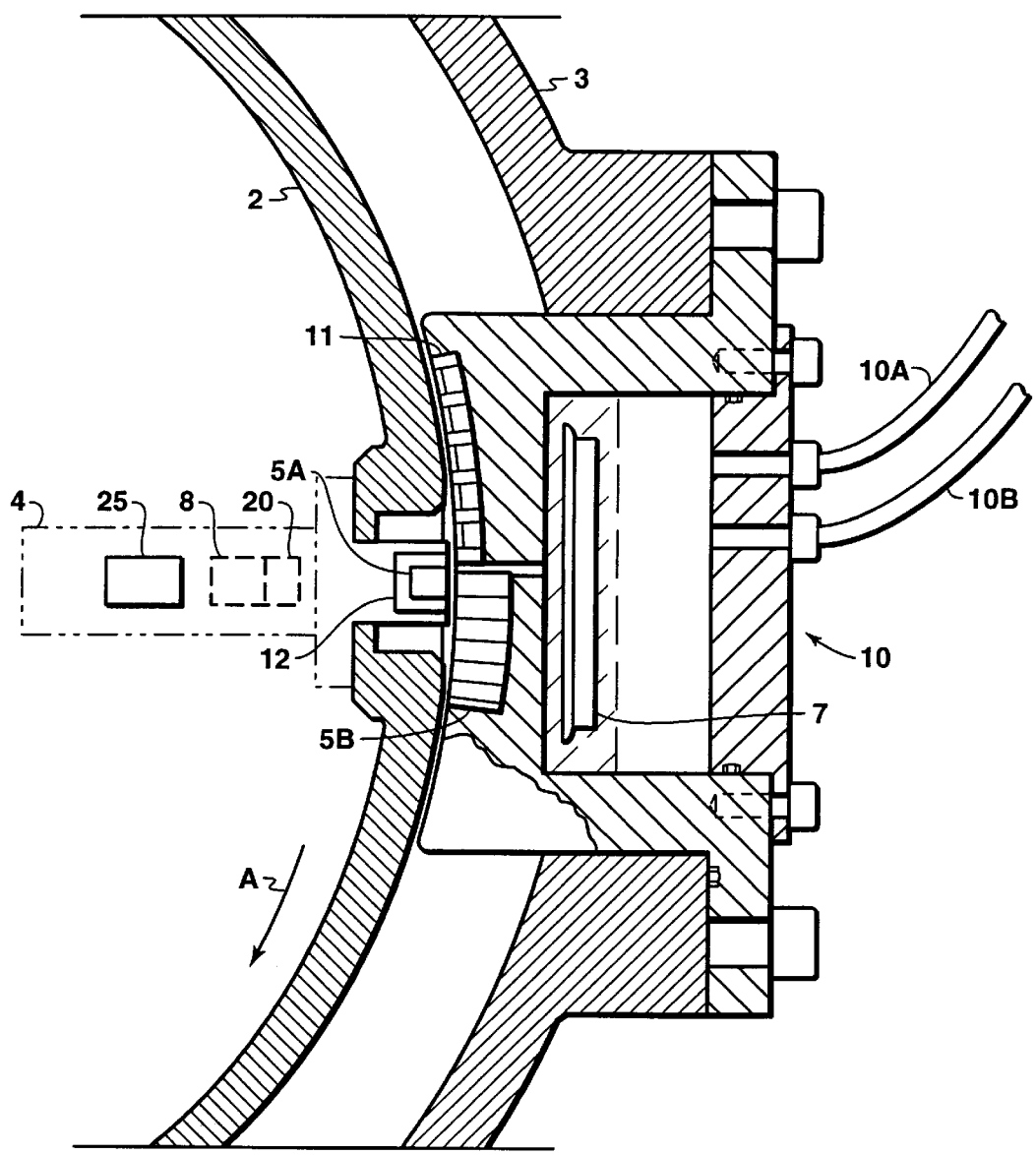
Figure 4:
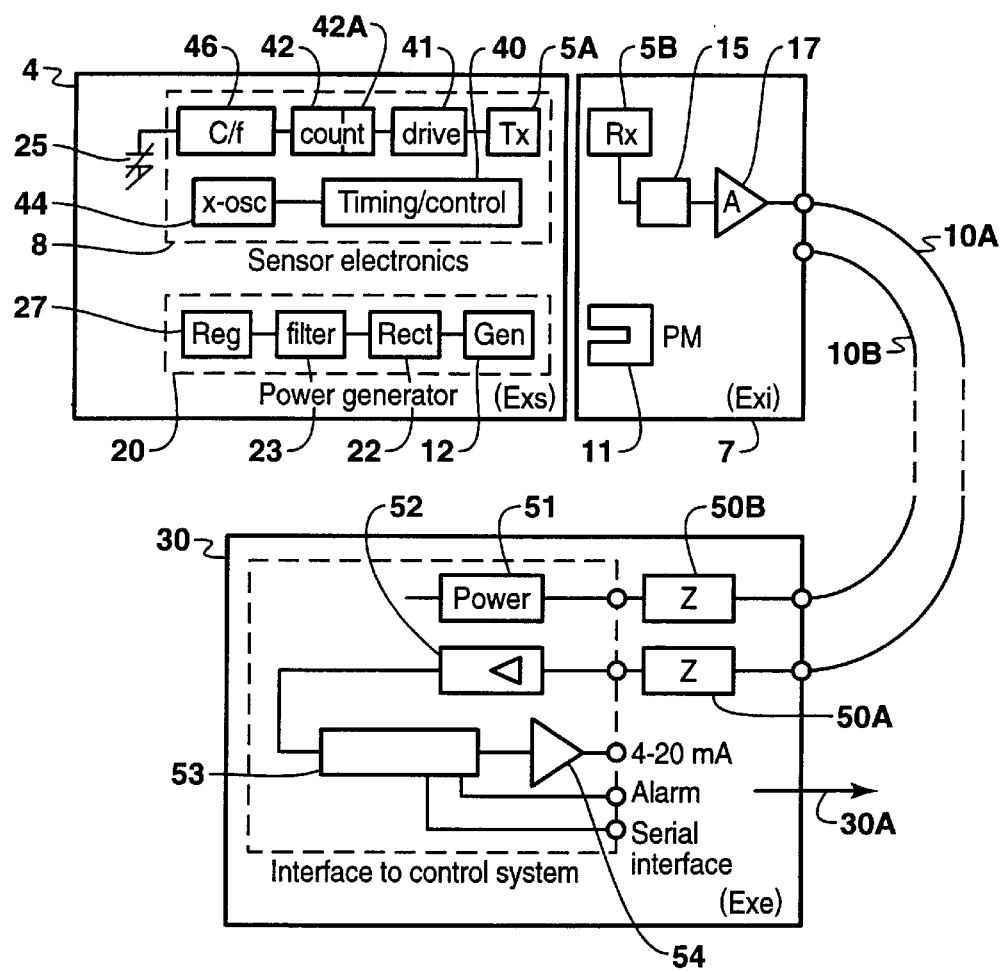
Figure 5:
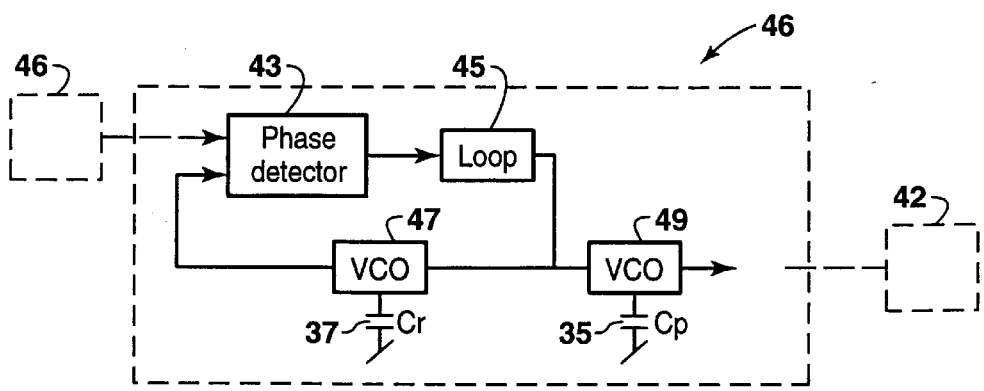
Figure 7:
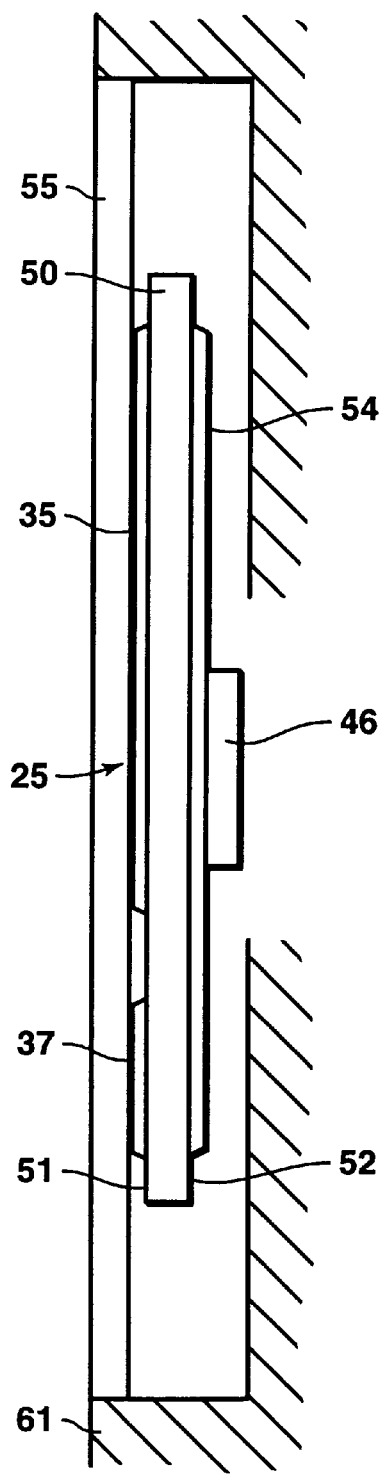

In the following description, the invention shall be explained more closely with reference to the drawings, in which:

FIG. 1 schematically and in principle illustrates the function of an apparatus according to the invention, associated with a centrifuge, FIG. 2 in enlarged cross-sectional view shows a part of the centrifuge housing and the rotor in FIG. 1, with the associated measurement apparatus, FIG. 3 schematically shows important components in an embodiment of the sensor in the measurement apparatus according to FIGS. 1 and 2, with three surrounding fluids, i.e. water, oil and gas, FIG. 4 shows a simplified electrical system or block diagram of the whole measurement apparatus as illustrated in FIG. 1, FIG. 5 schematically shows a particularly advantageous oscillator circuit which can be used in the system of FIG. 4, FIG. 6 shows an example of a practical embodiment of a sensor, partially in cross-sectional view and partially in longitudinal section, and FIG. 7 shows a much enlarged and cross-sectional view of a capacitive measuring element which can be incorporated in a sensor as illustrated, inter alia, in FIG. 6.

FIG. 1 shows a portion of the circumference of a centrifuge rotor 2 being provided with two measuring sensors 4 and 4'. Preferably these sensors are located at an angular spacing of 180° from each other, i.e. diametrically opposite in the rotor. It is obvious that the number of sensors in a centrifuge rotor can be one, two or more. An interface 1X between two fluids in the rotor 2 is also indicated in FIG. 1. In the sensor 4 there is schematically shown a measuring element 25 which can be adapted to measure the position of the interface 1X. Further, in the sensor 4 there is shown a block 8 which represents an electronic circuit. At one side this circuit is connected to the measuring element 25 and at the other side to one part 5A of a transmission device for measurement signals from the sensor 4 to a stationary measuring unit. In FIG. 1 the stationary measuring unit is shown as a block 7 in a measuring housing 10 which also comprises another part 5B of the transmission device just mentioned, as well as a magnet device 11 which is incorporated in a generator, as will be described more closely below with reference to FIG. 2.

For simplicity, the sensor 4 in FIG. 1 is shown with only one measuring element 25 for measuring the position of an interface 1X, but as will appear from the following description, it can be an advantage in practice for the primary use in water-oil-gas separation to employ two measuring element parts at a mutual spacing in the longitudinal direction of the sensor, i.e. at different radial positions in the centrifuge rotor 2.

The measuring unit 7 in housing 10 according to FIG. 1 is connection to an external control or regulating system 30 which comprises at least one output 30A to control equipment for the centrifuge.

FIG. 2 somewhat more in detail and in cross-section shows the centrifuge rotor and the cylindrical wall 2 thereof, as well as a surrounding housing 3. As in FIG. 1 the sensor 4 in FIG. 2 is shown schematically with the measuring element 25, the electronic circuit 8 and more specifically the transmission part or head 5A which is located at the end of sensor 4 which approaches the outer circumference of rotor 2. Thus, in this embodiment the sensor 4 is mounted in a bore in the rotor wall 2 so that the radially outer end of the sensor 4 comprising, inter alia, the transmission head 5A, can cooperate with stationary members or devices located in the measuring housing 10, which for example by means of bolts is attached to the centrifuge housing 3. In addition to the head 5A there is also shown in the end portion of sensor 4 a coil 12 which is incorporated in the generator device mentioned above, and which like head 5A is electrically connected to the electronic circuit 8.

The measuring unit 7 in FIG. 2 as illustrated can comprise a board or substrate carrying the necessary circuits with electronic components and connections. Also the stationary transmission head 5B adapted to cooperate with head 5A in sensor 4, can be considered to belong to measuring unit 7.

The arrow A in FIG. 2 indicates the direction of rotation of rotor 2. In front of the stationary head 5B as seen in the rotational direction there are arranged a row of magnets 11, being preferably permanent magnets, for cooperation with the coil 12 at the end portion of the sensor 4. Accordingly, when the rotor 2 rotates and because of the magnets 11, there will be induced a voltage in coil 12, and thereby a sufficient amount of electrical energy will be generated, for supplying the electronic circuit 8 for the operation thereof. Such power supply is necessary because the electronic circuit 8 comprises active elements adapted to store measurement values being recorded by measuring element 25 during rotation.

It is preferred that coil 12 is wound on a ferrite core. When the sensor moves past the permanent magnets 11 there will be generated an alternating current in the coil. In a manner known per se this alternating current can be rectified and filtered before it is applied to the electronic circuit 8. These components in a circuit 20 which is comprised by the generator device, shall be discussed more closely below in connection with FIG. 4.

It is clear that the high rotational speed, which can involve a linear velocity of the rotor circumference of 100 m/s, to a high degree contributes to a sufficient induced voltage and thereby generated power in the generator device as a whole.

Of great significance in this connection is also the gap or spacing between the outer rotor wall 2 with the sensor end portion comprising the head 5A and the coil-ferrite core 12, and the adjacent curved surface of measuring housing 10, in particular the permanent magnets 11 therein. For example the air gap can be of an order of magnitude of 2 mm. The basic function of the arrangement described here however, will be the same and in practice fully possible also with a somewhat wider gap.

An additional important factor in this connection is the fact that the row of permanent magnets 11 has a certain extension in the circumferential direction with respect to the rotor rotation, namely so that the magnet device 11 has a significantly larger extension in the circumferential direction than the cooperating coil 12 with its associated ferrite core. Therefore the electrical power supply for the electronic circuit 8 takes place over a distance corresponding broadly to the length of the magnet device 11 in the circumferential direction. This constitutes only a very small fraction of the whole circumference, but as will be explained more closely below with reference to FIG. 4, the electronic circuit 8 comprises means for storing the electrical energy from the generator during a sufficiently long time for the required operation of the electronic components.

The transmission or receiver head 5B is correspondingly extended in the circumferential direction like the magnet device 11, as will be seen from FIG. 2. This contributes to facilitating the signal transmission from the transmitter head 5A in rotor 2 during the high speed rotation thereof past head 5B. In view of a possible disturbance or influence on receiver head 5A from the main parts 11 and 12 of the generator device, it is an advantage according to a particular embodiment, that the magnetic field direction for the inductive transmission between heads 5A and 5B, is normal to the magnetic field direction in generator device 11–12.

Advantageously, both magnetic heads 5A and 5B in the transmission device can comprise ferrite cores, such as a row of U-cores arranged in receiver head 5B.

For the primary and specific use in centrifuges for separation of water, oil and gas, it is important that the complete apparatus and structure has an explosion-safe design. A safety precaution in this connection is to let the power supply from generator device 11–12 to electronic circuit 8 take place through zener barriers (not shown). Another design feature aiming at such safety, is potting of the electrical and electronic components, which also leads to increased reliability and secure operation.

From measuring housing 10 in FIG. 2 there are shown two leads or cables 10A and 10B for conveying transmitted and possibly somewhat processed measurement signals to the above mentioned control or regulating system 30, which is shown schematically in FIG. 1, where the connection 10A–B corresponds to the leads or cables just mentioned.

FIG. 3 illustrates somewhat more in detail but anyhow schematically, the components being incorporated in sensor 4 in a practical embodiment thereof. One end (to the left in FIG. 3) of sensor 4 is mounted in the rotor wall 2 and projects (to the right) into three fluids 1A, 1B and 1C which because of the rotation are separated into layers as shown. Thus, in the example concerned fluid 1A can be water, and fluid 1B oil, with an intermediate interface 1X as mentioned above. Between the oil layer 1B and the third fluid 1C which is here a gas, there is another interface 1Y.

In sensor 4 there is shown a first capacitive measuring element 25 for the position of the interface 1X, and a second capacitive measuring element 26 for the interface 1Y. The magnetic transmitter head 5A and the generator coil 12 are shown at the radially outer end of sensor 4, i.e. the end which is mounted in rotor wall 2. Coil 12 is connected to generator circuit 20.

In a purely block schematic manner there is for sensor 4 in FIG. 3 shown components or blocks incorporated in electronic circuit 8, i.e. in the first place a transmitter circuit 41 and a frequency counter 42 being responsive to a capacitance value from measuring elements 25 and 26. In the second place there are shown a crystal oscillator 44 and two further oscillator circuits 46 and 48 being each associated with a measuring element 25 and 26, respectively.

Measuring element 25 for the water-oil interface 1X will have a varying capacitance dependent upon how large proportion of the surface area of the measuring element against the fluids, is covered with water, since the water 1A as indicated in FIG. 3, constitutes one of the two electrodes in a capacitor formed by measuring elements 25. In measuring element 26 however, there are incorporated two permanent capacitor plates or electrodes, whereby the intermediate dielectric to a larger or smaller degree consists of oil or gas, so that the difference in dielectric constant between oil and gas leads to variations in the capacitance value of measuring element 26.

The electronic main components being shown in a simplified way in the arrangement of FIG. 3, are illustrated somewhat more in detail in FIG. 4, where the main parts of the measurement apparatus in the form of sensor 4, measuring unit 7 and external control system 30, can be seen.

Measurement values represented by the capacitance of measuring element 25 serves as an input signal to electronic circuit 8, which comprises a capacitance-frequency converter 46, frequency counter 42, which possibly can incorporate a processing part 42A, the drive or transmitter circuit 41 and the actual transmitter magnetic head 5A. Besides, the circuit 8 comprises the reference oscillator 44 which preferably is crystal controlled, and moreover a time control circuit 40.

A preferred embodiment of the capacitance-frequency converter 46 is shown somewhat more in detail in FIG. 5. As shown therein, the converter circuit can be considered to constitute a self-compensating oscillator based on a phase-locked loop. This includes a phase detector 43, a filter 45 and two identical voltage controlled oscillators 47 and 49, each being responsive to a separate measuring capacitor, namely the reference element or capacitor 37 and the measuring capacitor 35 respectively, in measuring element 25 as shown for example in FIG. 3. A converter circuit 48 corresponding fully to circuit 46 is provided for measuring element 26. For the sake of clarity only converter circuit 46 is shown in FIG. 4.

The manner of operation of the circuits described can be explained briefly as follows: The capacitive elements are frequency-determining elements in the self-compensating oscillator or converter circuit 46, and in counter circuit 42 the frequency is converted to a digital output signal upon counting of the frequency during an exactly determined time interval. The generation of the digital output signal, possibly combined with further signal processing, can be considered to take place in the processing part 42A shown, which can be more or less integrated with the frequency counter 42.

The exact determination of the counting period or interval takes place by means of crystal oscillator 44. The capacitive measuring element, such as element 35 at a given capacitance value will result in an output frequency from the oscillator depending on ambient temperature, supply voltage and ageing of circuit components being incorporated. In order to compensate for such and other sources of error, use is made of the two identical oscillators 47 and 49, being connected to the reference capacitive element 37 and the measuring capacitor element 35 respectively, as mentioned above. Ideally the output frequency of oscillator 47 is stable, except for possible unwanted drift. If the two oscillators 47 and 49 can be regarded as identical and being preferably built on the same silicon chip, it can be assumed that the drift will also be identical for the two oscillator circuits. Variations in the output frequency from the "stable" oscillator 47 can therefore be used to compensate for drift in the measuring oscillator 49. Best results with respect to stability are obtained with two voltage controlled oscillator circuits 47 and 49, of which the reference oscillator 47 is incorporated in the phase-locked loop mentioned above (FIG. 5) against a reference frequency from crystal oscillator 44. Thereby a compensated working point is established for the measuring oscillator 49.

For transmitting the measurement signals obtained, to measuring unit 7 in short time during movement of sensor 4 past the measuring unit 7, it is preferred to convert the measurement signals to digital words as already mentioned. A word length of 12 bits has been found to be suitable. This makes possible a maximum resolution of 4096 steps, which is more than sufficient. In actual practice electronic circuit 8 comprises three parallel frequency-digital converters, i.e. for water level, oil level and temperature respectively, since it is also of interest to measure the temperature of the fluid mentioned, in a centrifuge rotor during operation. The three resulting digital words of 12 bits each, are read out consecutively through magnetic heads 5A and 5B as previously described.

Storing of measurement values being recorded through at least a proportion of a resolution of the centrifuge rotor, is effected by controlling the counting interval, which can for example constitute 10% less than the time for a complete revolution. Accordingly, the output level will represent an average value of the various levels of the fluids in the centrifuge, measured over 90% of the centrifuge circumference. Details regarding the associated digital signal processing in this connection, will be apparent to experts in the field and will not be discussed more in detail here. In order to secure that the signal transmission from the rotor takes place at a correct angular position, a starter pulse is derived from the generator device 11–12 so as to indicate movement past the last permanent magnet 11.

Concerning the generator circuit in connection with coil 12, FIG. 4 shows a rectifier bridge 22, a filter 23 and a voltage regulator 27.

Measuring unit 7 comprises a discriminator circuit 15 between magnetic head 5B and a line driver or amplifier circuit 17, for conveying the digital measurement signals further along a lead 10A to the control system 30. From control system 30 the lead 10B conducts electrical power to measuring unit 7. Preferably zener barriers 50A and 50B are utilized in the control system 30 against the connecting leads 10A and 10B for measuring unit 7. This is preferred in view of the risk of explosion. In the control system or block 30 there are moreover included circuits being more or less near at hand, such as a current supply circuit 51, an amplifier circuit 52 and a microcontroller or processor 53 as well as an additional amplifier 54, whereby an electrical interface is indicated at 55 for connections to controls, alarms and so forth associated with the operation of the centrifuge.

In the example of a more practical embodiment of a sensor design as shown in FIG. 6 with accompanying cross-sectional views 6A and 6B as well a longitudial sectional view 6C, sensor 4 has an encasing 61 with a streamlined outer cross-sectional shape as will appear from the crossection FIGS. 6A and 6B. The cross-sectional shape here corresponds to a flow of the fluids in the axial direction of rotor 2.

In FIG. 6 the same three fluids 1A, 1B and 1C are shown as in FIG. 3 At the two interfaces between the fluids there is here in particular indicated examples of maximum levels, namely 1Xmax and 1Ymax respectively, as well as minimum levels, namely 1Xmin and 1Ymin respectively. As seen from FIG. 6 measuring element 25 comprises a capacitive electrode member or surface 35 adapted to cover the range of variation (1Xmin–1Xmax) of interface 1X between fluids 1A and 1B, and besides a reference electrode 37 adapted to be always located in the outer fluid 1A during operation of the centrifuge. Quite correspondingly measuring element 26 has a measuring part or electrode surface 31 for the interface 1Y between fluids 1B and 1C, and a reference electrode 32 adapted to be immersed in fluid 1B during operation. This arrangement with reference electrodes 32 and 37 according to the invention constitutes an advantageous solution for the purpose of eliminating certain sources of error. This has been explained already above with reference to the block diagram of FIG. 4.

FIG. 6A in cross-sectional view shows how the measuring element 26 is arranged in relation to a through-running slit 36 in sensor 4, corresponding to the axial flow direction through the rotor as mentioned above, whereby the two fluids 1B and 1C concerned, i.e. oil and gas respectively, in the primary field of use as mentioned, will enter into the slit 63 without displacement or unfavourable influence of the interface position to be measured, because of the flow through slit 63. The above fixed electrodes in measuring element 26 are located each on one and the other side of slit 63.

The cross-sectional view of FIG. 6B shows the measuring element 25 which faces outwards from one side wall of encasing 61 for direct cooperation with the surrounding fluid 1A, for example water, or fluid 1B which in the present example is oil. Behind measuring element 25 in FIG. 6B the above electronic circuit 8 has been shown purely schematically and located within an inner cavity in encasing 61. See also the corresponding location in the longitudinal section of FIG. 6C. The sensor encasing or housing 61 can be manufactured conveniently by casting of titanium, which combines strength and low weight.

Finally FIG. 7 at an enlarged scale shows an embodiment of the capacitive measuring element 25 mounted at a surface of encasing 61, which is here shown only partially and in cross-section. Measuring element 25 is built up on a plate-shaped substrate 50, preferably a ceram or other stable material. On the main surface 51 facing outwards, substrate 50 is provided in the first place with an electrode element or coating 35, as already explained above, and besides with a reference electrode coating 37. This arrangement substantially corresponds to what is also shown with respect to measuring element 25 in FIG. 6. The opposite main surface 52 of substrate 50 preferably as a conductive coating 54 which constitutes a ground plane. This contributes to making the whole measuring element 25 more well defined as to electrical conditions and also independent of the surroundings in encasing 61.

In front of the electrode coatings 35 and 36 and preferably intimately engaging these there is provided an electrically insulating plate 55 as a window against the fluids surrounding the sensor encasing 61. As discussed above the most frequent employment of the sensor will involve the presence of oil or water at the outside of plate 55. In such practical use the plate will be subjected to very severe external stresses, such as the very high pressures mentioned above, wear because of particles which may be contained in the fluids, and a high G-load. A preferred material in plate 55 is sapphire, which is wear-resistant and has the required mechanical strength in this measuring element structure.

The manner of operation of such a capacitive measuring element has been discussed already above, whereby a larger or smaller water coverage of the electrode 35 results in larger or smaller effective capacitor areas with the intermediate plate 55 as the dielectric. It may be an advantage to let the electrode 35 have a surface shape with a tapering width so that the capacitance variation will be linear in relation to changes of water level, i.e. the position of the interface between water and oil.

We claim:

1. Apparatus for measurement of the position of an interface between two fluids in a centrifuge rotor (2) during rotation, comprising an electric or magnetic sensor (4) mounted internally on a wall in the centrifuge rotor (2), and means (5A,5B) for contact-free and intermittent transmission of measurement signals from the sensor (4) to a stationary measuring unit (7) outside the centrifuge rotor, characterized in that the sensor (4) has such an extension in the radial direction of the rotor (2) that the sensor penetrates said interface, that the sensor (4) comprises an active electronic circuit (8) adapted to store measurement values that are recorded during at least a portion of a revolution of the rotor (2), before said transmission of corresponding measurement signals to the measuring unit (7), and that electric power supply to the electronic circuit (8) is provided for by generator means comprising a stationary magnet (11) near the centrifuge rotor (2) and a coil (12) mounted in the rotor so that a voltage is induced in the coil (12) during movement past the magnet (11) by rotation of the rotor (2), and the coil (12) is connected to the electronic circuit (8).

2. Apparatus according to claim 1, characterized in that the electronic circuit (8) comprises means (42A,46) for performing a certain signal processing based on said measurement values, preferably in order to form at least one digital word for said transmission to the measuring unit (7). (FIG. 4).

3. Apparatus according to claim 1, characterized in that capacitive measurement in the sensor (4) is adapted to be converted to frequency variation in said electronic circuit (8), which comprises a frequency counter (42) controlled by a clock oscillator (44) which determines the counting period (s). (FIG. 4).

4. Apparatus according to claim 3, characterized in that the clock oscillator (44) is also a reference oscillator for the capacitive measurement (46) with resulting frequency variations, so that instability in the clock oscillator is compensated for. (FIG. 4).

5. Apparatus according to claim 1, characterized in that the sensor (4) comprises a measuring part (35,31) for said interface (1X,1Y) and a reference part (37,32) adapted to be influenced only by one fluid (1A,1B). (FIGS. 6 and 7).

6. Apparatus according to claim 4, in particular for measuring the interface between two liquid fluids, characterized in that a capacitive measuring element (25) in the sensor (4) comprises a plate-shaped substrate (50) of a stable material, such as a ceram, one main surface (51) of which, being adapted to face towards the two fluids (1A,1B,1C), carries a capacitive measuring electrode element (35) and possibly a capacitive reference electrode element (37), whereas the opposite main surface (52) of the substrate (50) is preferably provided with a ground plane coating (54). (FIG. 7).

7. Apparatus according to claim 6, characterized in that in front of the measuring electrode element (35) and possibly the reference electrode element (37), there is provided an electrically insulating plate (55) of a wear resistant and mechanically strong material, preferably sapphire. (FIG. 7).

8. Apparatus according to claim 1, characterized in that the transmission of measurement signals takes place inductively by means of a magnetic transmitter head (5A) on the centrifuge rotor (2) and a cooperating magnetic receiver head (5B) provided on the measuring unit (7). (FIGS. 1 and 2).

9. Apparatus according to claim 8, characterized in that the receiver head (5B) is substantially more elongate in the circumferential direction than is the transmitter head (5A). (FIG. 2).

10. Apparatus according to claim 1, characterized in that the stationary magnet of said generator means comprises at least one permanent magnet and preferably a number of permanent magnets (11) in succession in the circumferential direction. (FIG. 2).

11. Apparatus according to claim 8, characterized in that the magnetic field direction for the inductive transmission (5A,5B) of measurement signals, is oriented substantially at right angles to the magnetic field direction of said generator means (11,12). (FIG. 2).

12. Apparatus according to claim 1, characterized in that the sensor (4) has an encasing (60,70) with a streamlined outer cross-sectional shape (61,71) with respect to a flow of the fluids in the axial direction of the centrifuge rotor (2). (FIG. 6).

* * * * *